(12) United States Patent
Senn et al.

(10) Patent No.: US 8,673,813 B2
(45) Date of Patent: Mar. 18, 2014

(54) PESTICIDE

(75) Inventors: Robert Senn, Basel (CH); Peter Maienfisch, Rodersdorf (CH); Peter Wyss, Souboz (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 315 days.

(21) Appl. No.: 10/801,405

(22) Filed: Mar. 16, 2004

(65) Prior Publication Data

US 2004/0176369 A1 Sep. 9, 2004

Related U.S. Application Data

(60) Division of application No. 09/716,656, filed on Nov. 20, 2000, now Pat. No. 6,867,169, which is a continuation of application No. 09/171,700, filed on Nov. 13, 1998, now abandoned.

(51) Int. Cl.
*A01N 25/26* (2006.01)
*A01N 43/02* (2006.01)

(52) U.S. Cl.
USPC .......................................... 504/100; 504/140

(58) Field of Classification Search
USPC ........................................ 504/132; 514/229.2
See application file for complete search history.

(56) References Cited

U.S. PATENT DOCUMENTS

| | | | |
|---|---|---|---|
| 5,140,019 A | 8/1992 | Wada et al. | 514/89 |
| 5,260,312 A | 11/1993 | Wada et al. | 514/342 |
| 5,521,176 A | 5/1996 | Wada et al. | 514/226.8 |
| 5,614,182 A | 3/1997 | Davidson et al. | |
| 5,852,012 A * | 12/1998 | Maienfisch et al. | 514/229.2 |
| 5,952,358 A | 9/1999 | Meunier et al. | |
| 5,994,331 A | 11/1999 | Erdelen et al. | |
| 6,001,858 A | 12/1999 | Sirinyan et al. | |
| 6,060,489 A | 5/2000 | Erdelen et al. | |
| 6,077,860 A | 6/2000 | Meunier et al. | |
| 6,218,407 B1 | 4/2001 | Erdelen et al. | |

FOREIGN PATENT DOCUMENTS

| | | |
|---|---|---|
| CA | 2100924 | 1/1994 |
| EP | 0 627 165 | 12/1994 |
| EP | 796042 | 9/1997 |
| JP | 07224062 | * 8/1995 |
| JP | 08291171 | * 11/1996 |
| WO | 9512314 | 5/1995 |
| WO | WO 95/33380 | 12/1995 |
| WO | WO 9617520 | 6/1996 |
| WO | WO 9623411 | 8/1996 |
| WO | WO 9637105 | 11/1996 |

OTHER PUBLICATIONS

Baranowski, Avermectins, Materialy Sesji Naukowei Instytutu Ochrony Roslin, 1002, vol. Date 1991, 31 (1), 214-20. (ABS).*
The Agrochemicals Handbook, A0891 / Aug. 1991.*
Derwent Abstracts 96-032163 [04], FR 2 720 230 , Dec. 1, 1995.
Derwent Abstracts 95-325540, JP 07224062 (1995).
Derwent Abstracts 95-048729/07, JP 06329508 (1993).
Derwent Abstracts 88-188016/27, JP 63126806 (1988).
Derwent Abstracts 91-104761, JP 03041005 (1991).
Derwent Abstracts 88-188014/27, JP 63126804 (1988).
Dekeyser et al., Brighton Crop Protection Conference—Pests & Diseases, "Novel Agent to Control Spider Mites" 5A-7, 99.487-492 (1996).
Harder et al., Brighton Crop Protection Conference—Pests & Diseases, "DPX-MP062: A Novel Broad-Spectrum, Environmentally Soft, Insect Control Compound", 5A-1, pp. 449-454 (1996).
Lee et al., Brighton Crop Protection Conference—Pests & Diseases, "A New Selective Insecticide for Caterpillar Control", 5A-6, pp. 481-486 (1996).
Tomlin, The Pesticide Manual, 10th Edition, British Crop Protection Council, Farnham, GB, XP 002038908, pp. 1335-1341 (1995).
Marshall, S.A., "Insects—their Natural History and Diversity; with a photographic guide to insects of eastern North America", 2006; Firefly Books; New York, pp. 585-587.
Species Tetranychus urticae—Twospotted Spider Mite; Bugguide. net, hosted by Iowa State University Entomology; Found at: http://bugguide.net/node/view/187589/tree?printable=1 on Feb. 27, 2013.

* cited by examiner

*Primary Examiner* — Alton Pryor
(74) *Attorney, Agent, or Firm* — James Cueva

(57) ABSTRACT

Composition for controlling insects and representatives of the order Acarina, which comprises a combination of variable amounts of one or more compounds of the formula

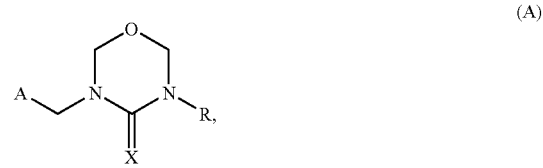

(A)

in which
A is an unsubstituted or, depending on the possibility of substitution on the ring system, mono- to tetrasubstituted, aromatic or non-aromatic monocyclic or bicyclic heterocyclic radical, in which the substituents of A can be chosen from the group consisting of $C_1$-$C_3$alkyl, $C_1$-$C_3$alkoxy, halogen, halo-$C_1$-$C_3$alkyl, cyclopropyl, halocyclopropyl, $C_2$-$C_3$alkenyl, $C_2$-$C_3$alkynyl, halo-$C_2$-$C_3$alkenyl, halo-$C_2$-$C_3$alkynyl, halo-$C_1$-$C_3$alkoxy, $C_1$-$C_3$alkylthio, Halo-$C_1$-$C_3$alkylthio, allyloxy, propargyloxy, allylthio, propargylthio, haloallyloxy, haloallylthio, cyano and nitro;
R is hydrogen, $C_1$-$C_6$alkyl, phenyl-$C_1$-$C_4$alkyl, $C_3$-$C_6$cycloalkyl, $C_2$-$C_6$alkenyl or $C_2$-$C_6$alkynyl; and
X is N—$NO_2$ or N—CN,
in the free form or in salt form, if appropriate tautomers, in the free form or salt form, and one or more of the compounds (I) to (CLXXXIV) mentioned according to the invention and at least one auxiliary.
A method of controlling pests, a process for the preparation of the composition, its use and plant propagation material treated with it, and the use of the compound of the formula (A) for the preparation of the composition, are described.

4 Claims, No Drawings

PESTICIDE

This application is a divisional application of U.S. patent application Ser. No. 09/716,656, filed Nov. 20, 2000; which is a continuation of U.S. patent application Ser. No. 09/171,700, now abandoned; the contents of which are incorporated herein by reference.

The present invention relates to a composition which comprises a pesticidal active compound combination, a method for controlling pests with this composition, a process for the preparation of the composition, its use and plant propagation material treated with it, and the use of a compound of the following formula (A) for the preparation of the composition.

Certain mixtures of active compounds are proposed for pest control in the literature. However, the biological properties of these mixtures of known compounds are not completely satisfactory in the field of pest control, and for this reason there is a need to provide further mixtures having synergistic pest control properties, in particular for control of insects and representatives of the order Acarina. This object is achieved according to the invention by providing the present composition.

The invention accordingly relates to a composition for controlling insects and representatives of the order Acarina, which comprises a combination of variable amounts of one or more compounds of the formula

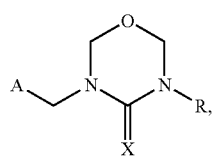

(A)

in which

A is an unsubstituted or, depending on the possibility of substitution on the ring system, mono- to tetrasubstituted, aromatic or non-aromatic monocyclic or bicyclic heterocyclic radical, in which the substituents of A are chosen from the group consisting of $C_1$-$C_3$alkyl, $C_1$-$C_3$alkoxy, halogen, halo-$C_1$-$C_3$alkyl, cyclopropyl, halocyclopropyl, $C_2$-$C_3$alkenyl, $C_2$-$C_3$alkynyl, halo-$C_2$-$C_3$alkenyl, halo-$C_2$-$C_3$alkynyl, halo-$C_1$-$C_3$alkoxy, $C_1$-$C_3$alkylthio, halo-$C_1$-$C_3$alkylthio, allyloxy, propargyloxy, allylthio, propargylthio, haloallyloxy, haloallylthio, cyano and nitro;

R is hydrogen, $C_1$-$C_6$alkyl, phenyl-$C_1$-$C_4$alkyl, $C_3$-$C_6$cycloalkyl, $C_2$-$C_6$alkenyl or $C_2$-$C_6$alkynyl; and X is N—$NO_2$ or N—CN, in the free form or in salt form, if appropriate tautomers, in the free form or salt form, and one or more of the compounds:

(I) aldicarb;
(II) azinphos-methyl;
(III) benfuracarb;
(IV) bifenthrin;
(V) buprofezin;
(VI) carbofuran;
(VII) dibutylaminothio;
(VIII) cartap;
(IX) chlorofluazuron;
(X) chloropyrifos;
(XI) cyfluthrin;
(XII) lambda-cy-halothrin;
(XIII) alpha-cypermethrin;
(XIV) zeta-Cypermethrin;
(XV) deltamethrin;
(XVI) diflubenzuron;
(XVII) endosulfan;
(XVIII) ethiofencarb;
(XIX) fenitrothion;
(XX) fenobucarb;
(XXI) fenvalerate;
(XXII) formothion;
(XXIII) methiocarb;
(XXIV) heptenophos;
(XXV) imidacloprid;
(XXVI) isoprocarb;
(XXVII) methamidophos;
(XXVIII) methomyl;
(XXIX) mevinphos;
(XXX) parathion;
(XXXI) parathion-methyl;
(XXXII) phosalone;
(XXXIII) pirimicarb;
(XXXIV) propoxur;
(XXXV) teflubenzuron;
(XXXVI) terbufos;
(XXXVII) triazamate;
(XXXVIII) abamectin;
(XXXIX) fenobucarb;
(XL) tebufenozide;
(XLI) fipronil;
(XLII) beta-cyfluthrin;
(XLIII) silafluofen;
(XLIV) fenpyroximate;
(XLV) pyridaben;
(XLVI) fenazaquin;
(XLVII) pyriproxyfen;
(XLVIII) pyrimidifen;
(XLIX) nitenpyram;
(L) NI-25, acetamiprid;
(LI) avermectin $B_1$ (abamectin);
(LII) a plant extract which is active against insects;
(LIII) a preparation which comprises nematodes which are active against insects;
(LIV) a preparation obtainable from *Bacillus subtilis*;
(LV) a preparation which comprises fungi which are active against insects;
(LVI) a preparation which comprises viruses which are active against insects;
(LVII) AC 303 630;
(LVIII) acephate;
(LIX) acrinathrin;
(LX) alanycarb;
(LXI) alphamethrin;
(LXII) amitraz;
(LXIII) AZ 60541;
(LXIV) azinphos A;
(LXV) azinphos M;
(LXVI) azocyclotin;
(LXVII) bendiocarb;
(LXVIII) bensultap;
(LXIX) betacyfluthrin;
(LXX) BPMC;
(LXXI) brofenprox;
(LXXII) bromophos A;
(LXXIII) bufencarb;
(LXXIV) butocarboxin;
(LXXV) butylpyridaben;
(LXXVI) cadusafos;
(LXXVII) carbaryl;
(LXXVIII) carbophenothion;
(LXXIX) chloethocarb;
(LXXX) chloroethoxyfos;
(LXXXI) chloromephos;
(LXXXII) cis-res-methrin;
(LXXXIII) clocythrin;
(LXXXIV) clofentezin;
(LXXXV) cyanophos;
(LXXXVI) cycloprothrin;
(LXXXVII) cyhexatin;
(LXXXVIII) demeton M;
(LXXXIX) demeton S;
(XC) demeton-S-methyl;
(XCI) dichlofenthion;

(XCII) dicliphos;
(XCIII) diethion;
(XCIV) dimethoate;
(XCV) dimethylvinphos;
(XCVI) dioxathion;
(XCVII) edifenphos;
(XCVIII) emamectin;
(XCIX) esfenvalerate;
(C) ethion;
(CI) ethofenprox;
(CII) ethoprophos;
(CIII) etrimphos;
(CIV) fenamiphos;
(CV) fenbutatin oxide;
(CVI) fenothiocarb;
(CVII) fenpropathrin;
(CVIII) fenpyrad;
(CIX) fenthion;
(CX) fluazinam;
(CXI) flucycloxuron;
(CXII) flucythrinate;
(CXIII) flufenoxuron;
(CXIV) flufenprox;
(CXV) fonophos;
(CXVI) fosthiazate;
(CXVII) fubfenprox;
(CXVIII) HCH;
(CXIX) hexaflumuron;
(CXX) hexythiazox;
(CXXI) iprobenfos;
(CXXII) isofenphos;
(CXXIII) isoxathion;
(CXXIV) ivermectin;
(CXXV) lambda-cyhalothrin;
(CXXVI) malathion;
(CXXVII) mecarbam;
(CXXVIII) mesulfenphos;
(CXXIX) metaldehyde;
(CXXX) metolcarb;
(CXXXI) milbemectin;
(CXXXII) moxidectin;
(CXXXIII) naled;
(CXXXIV) NC 184;
(CXXXV) omethoate;
(CXXXVI) oxamyl;
(CXXXVII) oxydemethon M;
(CXXXVIII) oxydeprofos;
(CXXXIX) permethrin;
(CXL) phenthoate;
(CXLI) phorate;
(CXLII) phosmet;
(CXLIII) phoxim;
(CXLIV) pirimiphos M;
(CXLV) pirimiphos A;
(CXLVI) promecarb;
(CXLVII) propaphos;
(CXLVIII) prothiofos;
(CXLIX) prothoate;
(CL) pyrachlophos;
(CLI) pyrada-phenthion;
(CLII) pyresmethrin;
(CLIII) pyrethrum;
(CLIV) RH 5992;
(CLV) salithion;
(CLVI) sebufos;
(CLVII) sulfotep;
(CLVIII) sulprofos;
(CLIX) tebufenpyrad;
(CLX) tebupirimphos;
(CLXI) tefluthrin;
(CLXII) temephos;
(CLXIII) terbam;
(CLXIV) tetrachlorovinphos;
(CLXV) thiafenox;
(CLXVI) thiodicarb;
(CLXVII) thiofanox;
(CLXVIII) thionazin;
(CLXIX) thuringiensin;
(CLXX) tralomethrin;
(CLXXI) triarthen;
(CLXXII) triazophos;
(CLXXIII) triazuron;
(CLXXIV) trichlorofon;
(CLXXV) triflumuron;
(CLXXVI) trimethacarb;
(CLXXVII) vamidothion;
(CLXXVIII) xylylcarb;
(CLXXIX) YI 5301/5302;
(CLXXX) zetamethrin;
(CLXXXI) DPX-MP062;
(CLXXXII) RH-2485;
(CLXXXIII) D2341; or
(CLXXXIV) XMC (3,5-xylyl-methylcarbamate), and at least one auxiliary.

Compounds of the formula (A) are described in EP-A-580553.

The compounds (I) to (CLXXXIV) are known to the expert. In particular (I) 2-methyl-2-(methylthio)propionaldehyde O-methylcarbamoyloxime (aldicarb) is known from The Pesticide Manual, 9$^{th}$ Ed. (1991), The British Crop Protection Council, London, page 16;

(II) S-3,4-dihydro-4-oxo-1,2,3-benzotriazin-3-ylmethyl O,O-dimethyl phosphorodithioate (azinphos-methyl) is known from The Pesticide Manual, 9$^{th}$ Ed. (1991), The British Crop Protection Council, London, page 46;

(III) ethyl N-[2,3-dihydro-2,2-dimethylbenzofurane-7-yloxycarbonyl(methyl)aminothio]-N-isopropyl-β-alaninate (benfuracarb) is known from The Pesticide Manual, 9$^{th}$ Ed. (1991), The British Crop Protection Council, London, page 57;

(IV) 2-methylbiphenyl-3-ylmethyl (Z)-(1RS)-cis-3-(2-chloro-3,3,3-trifluoroprop-1-enyl)-2,2-dimethylcyclopropanecarboxylate (bifenthrin) is known from The Pesticide Manual, 9$^{th}$ Ed. (1991), The British Crop Protection Council, London, page 73;

(V) 2-tert-butylimino-3-isopropyl-5-phenyl-1,3,5-thiadiazian-4-one (buprofezin) is known from The Pesticide Manual, 9$^{th}$ Ed. (1991), The British Crop Protection Council, London, page 105;

(VI) 2,3-dihydro-2,2-dimethylbenzofuran-7-yl methylcarbamate (carbofuran) is known from The Pesticide Manual, 9$^{th}$ Ed. (1991), The British Crop Protection Council, London, page 126;

(VII) 2,3-dihydro-2,2-dimethylbenzofuran-7-yl (dibutylaminothio)-methylcarbamate (carbosulfan) is known from The Pesticide Manual, 9$^{th}$ Ed. (1991), The British Crop Protection Council, London, page 129;

(VIII) S,S'-(2-dimethylaminotrimethylene) bis(thiocarbamate) (cartap) is known from The Pesticide Manual, 9$^{th}$ Ed. (1991), The British Crop Protection Council, London, page 132;

(IX) 1-[3,5-dichloro-4-(3-chloro-5-trifluoromethyl-2-pyridyloxy)phenyl]-3-(2,6-difluorobenzoyl)-urea (chlorfluazuron) is known from The Pesticide Manual, 9$^{th}$ Ed. (1991), The British Crop Protection Council, London, page 143;

(X) O,O-diethyl O-3,5,6-trichloro-2-pyridyl phosphorothioate (chloropyrifos) is known from The Pesticide Manual, 9$^{th}$ Ed. (1991), The British Crop Protection Council, London, page 166;

(XI) (RS)-α-cyano-4-fluoro-3-phenoxybenzyl (1RS)-cis-trans-3-(2,2-dichlorovinyl)-2,2-di-methylcyclopropanecarboxylate (cyfluthrin) is known from The Pesticide Manual, 9$^{th}$ Ed. (1991), The British Crop Protection Council, London, page 198;

(XII) Mixture of (S)-α-cyano-3-phenoxybenzyl Z-(1R)-cis-3-(2-chloro-3,3,3-trifluoropropenyl)-2,2-dimethylcyclopropanecarboxylate and (R)-α-cyano-3-phenoxybenzyl Z-(1S)-cis-3-(2-chloro-3,3,3-trifluoropropenyl)-2,2-dimethylcyclopropanecarboxylate (lambda-cyhalothrin) is known from The Pesticide Manual, $9^{th}$ Ed. (1991), The British Crop Protection Council, London, page 203;

(XIII) Racemate of (S)-α-cyano-3-phenoxybenzyl (1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate (alpha-cypermethrin) is known from The Pesticide Manual, $9^{th}$ Ed. (1991), The British Crop Protection Council, London, page 210;

(XIV) A mixture of (S)-α-cyano-3-phenoxybenzyl (1RS)-3-(2,2-dichlorovinyl)-2,2-di-methylcyclopropanecarboxylate and (S)-α-cyano-3-phenoxybenzyl (3RS)-3-(2,2-dichlorovinyl)-2,2-dimethylcyclopropanecarboxylate (zeta-cypermethrin) is known from The Pesticide Manual, $10^{th}$ Ed. (1994), The British Crop Protection Council, London, page 265;

(XV) (S)-α-cyano-3-phenoxybenzyl (1R)-cis-3-(2,2-dibromvinyl)-2,2-dimethylcyclopropanecarboxylate (deltamethrin) is known from The Pesticide Manual, $9^{th}$ Ed. (1991), The British Crop Protection Council, London, page 232;

(XVI) (4-chlorophenyl)-3-(2,6-difluorobenzoyl)urea (diflubenzuron) is known from The Pesticide Manual, $9^{th}$ Ed. (1991), The British Crop Protection Council, London, page 281;

(XVII) (1,4,5,6,7,7-hexachloro-8,9,10-trinorborn-5-en-2,3-ylenebismethylene)sulfite (endosulfan) is known from The Pesticide Manual, $9^{th}$ Ed. (1991), The British Crop Protection Council, London, page 332;

(XVIII) α-ethylthio-o-tolyl methylcarbamate (ethiofencarb) is known from The Pesticide Manual, $9^{th}$ Ed. (1991), The British Crop Protection Council, London, page 343;

(XIX) O,O-dimethyl O-4-nitro-m-tolyl phosphorothioate (fenitrothion) is known from The Pesticide Manual, $9^{th}$ Ed. (1991), The British Crop Protection Council, London, page 369;

(XX) 2-sec-butylphenyl methylcarbamate (fenobucarb) is known from The Pesticide Manual, $9^{th}$ Ed. (1991), The British Crop Protection Council, London, page 371;

(XXI) (RS)-α-cyano-3-phenoxybenzyl (RS)-2-(4-chlorophenyl)-3-methylbutyrate (fenvalerate) is known from The Pesticide Manual, $9^{th}$ Ed. (1991), The British Crop Protection Council, London, page 388;

(XXII) [formyl(methyl)carbamoylmethyl] O,O-dimethyl phosphorodithioate (formothion) is known from The Pesticide Manual, $9^{th}$ Ed. (1991), The British Crop Protection Council, London, page 440;

(XXIII) 4-methylthio-3,5-xylyl methylcarbamate (methiocarb) is known from The Pesticide Manual, $10^{th}$ Ed. (1994), The British Crop Protection Council, London, page 677;

(XXIV) 7-chlorobicyclo[3.2.0]hepta-2,6-dien-6-yl dimethylphosphate (heptenophos) is known from The Pesticide Manual, $9^{th}$ Ed. (1991), The British Crop Protection Council, London, page 467;

(XXV) (6-chloro-3-pyridylmethyl)-N-nitroimidazolidin-2-ylidenamine (imidacloprid) is known from The Pesticide Manual, $9^{th}$ Ed. (1991), The British Crop Protection Council, London, Page 491;

(XXVI) 2-isopropylphenyl methylcarbamate (isoprocarb) is known from The Pesticide Manual, $9^{th}$ Ed. (1991), The British Crop Protection Council, London, Page 504;

(XXVII) O,S-dimethyl phosphoramidothioate (methamidophos) is known from The Pesticide Manual, $9^{th}$ Ed. (1991), The British Crop Protection Council, London, Page 563;

(XXVIII) S-methyl N-(methylcarbamoyloxy)thioacetimidate (methomyl) is known from The Pesticide Manual, $9^{th}$ Ed. (1991), The British Crop Protection Council, London, Page 570;

(XXIX) methyl 3-(dimethoxyphosphinoyloxy)but-2-enoate (mevinphos) is known from The Pesticide Manual, $9^{th}$ Ed. (1991), The British Crop Protection Council, London, Page 592;

(XXX) O,O-diethyl O-4-nitrophenyl phosphorothioate (parathion) is known from The Pesticide Manual, $9^{th}$ Ed. (1991), The British Crop Protection Council, London, Page 648;

(XXXI) O,O-dimethyl O-4-nitrophenyl phosphorothioate (parathion-methyl) is known from The Pesticide Manual, $9^{th}$ Ed. (1991), The British Crop Protection Council, London, Page 650;

(XXXII) S-6-chloro-2,3-dihydro-2-oxo-1,3-benzoxazol-3-ylmethyl O,O-diethyl phosphordithioate (phosalone) is known from The Pesticide Manual, $9^{th}$ Ed. (1991), The British Crop Protection Council, London, Page 674;

(XXXIII) 2-dimethylamino-5,6-dimethylpyrimidin-4-yl dimethylcarbamate (pirimicarb) is known from The Pesticide Manual, $9^{th}$ Ed. (1991), The British Crop Protection Council, London, Page 690;

(XXXIV) 2-isopropoxyphenyl methylcarbamate (propoxur) is known from The Pesticide Manual, $9^{th}$ Ed. (1991), The British Crop Protection Council, London, Page 727;

(XXXV) 1-(3,5-dichloro-2,4-difluorophenyl)-3-(2,6-difluorobenzoyl)urea (teflubenzuron) is known from The Pesticide Manual, $9^{th}$ Ed. (1991), The British Crop Protection Council, London, Page 790;

(XXXVI) S-tert-butylthiomethyl O,O-dimethyl phosphorodithioate (terbufos) is known from The Pesticide Manual, $9^{th}$ Ed. (1991), The British Crop Protection Council, London, Page 795;

(XXXVII) ethyl (3-tert.-butyl-1-dimethylcarbamoyl-1H-1,2,4-triazol-5-yl-thio)acetate (triazamate) is known from The Pesticide Manual, $10^{th}$ Ed. (1994), The British Crop Protection Council, London, Page 1006;

(XXXVIII) abamectin is known from The Pesticide Manual, $9^{th}$ Ed. (1991), The British Crop Protection Council, London, Page 3;

(XXXIX) 2-sec-butylphenyl methylcarbamate (fenobucarb) is known from The Pesticide Manual, $9^{th}$ Ed. (1991), The British Crop Protection Council, London, Page 371;

(XL) N-tert-butyl-N'-(4-ethylbenzoyl)-3,5-dimethylbenzohydrazide (tebufenozide) is known from The Pesticide Manual, $10^{th}$ Ed. (1994), The British Crop Protection Council, London, Page 943;

(XLI) (±)-5-amino-1-(2,6-dichloro-α,α,α-trifluoro-p-tolyl)-4-trifluoromethyl-sulfinylpyrazole-3-carbonitril (fipronil) is known from The Pesticide Manual, $10^{th}$ Ed. (1994), The British Crop Protection Council, London, Page 463;

(XLII) α-cyano-4-fluoro-3-phenoxybenzyl 3-(2,2-dichlorovinyl)-2,2-dimethylcyclopropane-carboxylate (beta-cyfluthrin) is known from The Pesticide Manual, $10^{th}$ Ed. (1994), The British Crop Protection Council, London, Page 250;

(XLIII) (4-ethoxyphenyl)[3-(4-fluoro-3-phenoxyphenyl)propyl](dimethyl)silane (silafluofen) is known from The Pesticide Manual, $10^{th}$ Ed. (1994), The British Crop Protection Council, London, Page 912;

(XLIV) tert-butyl (E)-α-(1,3-dimethyl-5-phenoxypyrazol-4-yl-methylenamino-oxy)-p-toluate (fenpyroximate) is known from The Pesticide Manual, 10th Ed. (1994), The British Crop Protection Council, London, Page 450;

(XLV) 2-tert-butyl-5-(4-tert.-butylbenzylthio)-4-chloropyridazin-3(2H)-one (pyridaben) is known from The Pesticide Manual, 10th Ed. (1994), The British Crop Protection Council, London, Page 879;

(XLVI) 4-tert-butylphenethyl quinazolin-4-yl ether (fenazaquin) is known from The Pesticide Manual, 10th Ed. (1994), The British Crop Protection Council, London, Page 426;

(XLVII) 4-phenoxyphenyl (RS)-2-(pyridyloxy)propyl ether (pyriproxyfen) is known from The Pesticide Manual, 10th Ed. (1994), The British Crop Protection Council, London, Page 887;

(XLVIII) 5-chloro-N-{2-[4-(2-ethoxyethyl)-2,3-dimethylphenoxy]ethyl}-6-ethylpyrimidin-4-amine (pyrimidifen) is known from The Pesticide Manual, 10th Ed. (1994), The British Crop Protection Council, London, Page 887;

(XLIX) (E)-N-(6-chloro-3-pyridylmethyl)-N-ethyl-N'-methyl-2-nitrovinylidenediamine (nitenpyram) is known from The Pesticide Manual, 10th Ed. (1994), The British Crop Protection Council, London, Page 736;

(L) (E)-$N^1$-[(6-chloro-3-pyridyl)methyl]-$N^2$-cyano-$N^1$-methylacetamidine (NI-25, acetamiprid) is known from The Pesticide Manual, 10th Ed. (1994), The British Crop Protection Council, London, Page 730;

(LI) avermectin $B_1$ (abamectin) is known from The Pesticide Manual, 10th Ed. (1994), The British Crop Protection Council, London, Page 1;

(LII) a plant extract which is active against insects, in particular (2R,6aS,12aS)-1,2,6,6a,12,12a-hexahydro-2-isopropenyl-8,9-dimethoxy-chromeno[3,4-b]furo[2,3-h]-chromen-6-one (rotenone), is known from The Pesticide Manual, 9th Ed. (1991), The British Crop Protection Council, London, Page 758; and an extract from *Azadirachta indica*, in particular azadirachtin, is known from The Pesticide Manual, 10th Ed. (1991), The British Crop Protection Council, London, Page 54; and (LIII) a preparation which comprises nematodes which are active against insects, preferably *Heterorhabditis bacteriophora, Heterorhabditis megidis* is known from The Pesticide Manual, 10th Ed. (1994), The British Crop Protection Council, London, Page 560; one comprising *Steinernema feltiae* is known from The Pesticide Manual, 10th Ed. (1994), The British Crop Protection Council, London, Page 920, and one comprising *Steinernema scapterisci* is known from The Pesticide Manual, 10th Ed. (1994), The British Crop Protection Council, London, Page 921;

(LIV) a preparation obtainable from *Bacillus subtilis* is known from The Pesticide Manual, 10th Ed. (1994), The British Crop Protection Council, London, Page 62; or one obtainable from a *Bacillus thuringiensis* strain, with the exception of compounds isolated from GC91 or from NCTC11821, is known;

(LV) a preparation which comprises fungi which are active against insects, preferably *Verticillium lecanii*, is known from The Pesticide Manual, 10th Ed. (1994), The British Crop Protection Council, London, Page 1040; one comprising *Beauveria brogniartii* is known from The Pesticide Manual, 10th Ed. (1994), The British Crop Protection Council, London, Page 69; and one comprising *Beauveria bassiana* is known from The Pesticide Manual, 10th Ed. (1994), The British Crop Protection Council, London, Page 69;

(LVI) a preparation which comprises viruses which are active against insects, preferably *Neodiprion sertifer* NPV, is known from The Pesticide Manual, 9th Ed. (1991), The British Crop Protection Council, London, Page 616; one comprising *Mamestra brassicae* NPV is known from The Pesticide Manual, 10th Ed. (1994), The British Crop Protection Council, London, Page 633; and one comprising *Cydia pomonella* granulosis virus is known from The Pesticide Manual, 10th Ed. (1994), The British Crop Protection Council, London, Page 247;

(CLXXXI) indeno[1,2-e][1,3,4]oxadiazine-4a (3H)-carboxylic acid, 7-chloro-2,5-dihydro-2-[[(methoxycarbonyl)[(4-trifluoromethoxy)phenyl]amino]carbonyl]-, methyl ester (DPX-MP062), is known from the Brighton Crop Protection Conference, 1996, 449-456;

(CLXXXII) N'-tert-butyl-N'-(3,5-dimethylbenzoyl)-3-methoxy-2-methylbenzohydrazide (RH-2485, methoxyfenozide) is known from the Brighton Crop Protection Conference, 1996, 481-486; and (CLXXXIII) N'-[4-methoxybiphenyl-3-yl]hydrazinecarboxylic acid isopropyl ester (D 2341) is known from the Brighton Crop Protection Conference, 1996, 487-493.

The compounds of the formula (A) can in some cases be in the form of tautomers. For example, if R is hydrogen, corresponding compounds of the formula (A), i.e. those having a 3-H-4-imino-perhydro-1,3,5-oxadiazine partial structure, can be in equilibrium with the particular tautomers which contain a 4-amino-1,2,5,6-tetrahydro-1,3,5-oxadiazine partial structure. Compounds of the formula (A) above and below are accordingly also to be understood as meaning, where appropriate, corresponding tautomers, even if the latter are not mentioned specifically in each case.

Compounds of the formula (A) which contain at least one basic centre can form, for example, acid addition salts. These are formed, for example, with strong inorganic acids such as mineral acids, for example perchloric acid, sulfuric acid, nitric acid, nitrous acid, a phosphoric acid or a hydrogen halide acid, with strong organic carboxylic acids, such as $C_1$-$C_4$alkanecarboxylic acids which are unsubstituted or substituted, for example by halogen, for example acetic acid, such as dicarboxylic acids which are saturated or unsaturated, for example oxalic, malonic, succinic, maleic, fumaric or phthalic acid, such as hydroxycarboxylic acids, for example ascorbic, lactic, malic, tartaric or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of the formula (A) with at least one acid group can furthermore form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propyl-amine, or a mono- di- or trihydroxy-lower alkylamine, for example mono-, di- or triethanolamine. If appropriate, corresponding inner salts can furthermore be formed. Agrochemically advantageous salts are preferred in the context of the invention. As a result of the close relationship between the compounds of the formula (A) in the free form and in the form of their salts, the free compounds of the formula (A) and their salts above and below are also appropriately and expediently to be understood as meaning, where appropriate, the corresponding salts and the free compounds of the formula (A). The same applies correspondingly to tautomers of compounds of the formula (A) and salts thereof. In each case the free form is in general preferred.

Compositions which comprise the compound of the formula (A) in the free form are preferred in the context of the present invention.

The general terms used above and below have the meanings given below, unless defined otherwise.

Heteroatoms in the cyclic base skeleton of the heterocyclic radical R are all elements of the Periodic Table which can form at least two covalent bonds. N and S are preferred.

Halogen—as a group per se and as a structural element of other groups and compounds, such as of haloalkyl, haloalkylthio, haloalkoxy, halocyclopropyl, haloalkenyl, haloalkynyl, haloallyloxy and haloallylthio—is fluorine, chlorine, bromine or iodine, in particular fluorine, chlorine or bromine, especially fluorine or chlorine, in particular chlorine.

Unless defined otherwise, carbon-containing groups and compounds in each case contain 1 up to and including 6, preferably 1 up to and including 3, in particular 1 or 2, carbon atoms.

Cycloalkyl is cyclopropyl, cyclobutyl, cyclopentyl or cyclohexyl, preferably cyclopropyl.

Alkyl—as a group per se and as a structural element of other groups and compounds, such as of phenylalkyl, haloalkyl, alkoxy, haloalkoxy, alkylthio and haloalkylthio—is, in each case taking into due consideration the number of carbon atoms, defined from case to case, contained in the corresponding group or compound, either straight-chain, i.e. methyl, ethyl, propyl, butyl, pentyl or hexyl, or branched, for example, isopropyl, isobutyl, sec-butyl, tert-butyl, isopentyl, neopentyl or isohexyl.

Alkenyl, haloalkenyl, alkynyl and haloalkynyl are straight-chain or branched and in each case contain two or preferably one unsaturated carbon-carbon bond(s). The double or triple bonds of this substituent are preferably separated from the remaining part of the compound of the formula (A) by at least one saturated carbon atom. Examples are allyl, methallyl, but-2-enyl, but-3-enyl, propargyl, but-2-ynyl and but-3-ynyl.

Halogen-substituted carbon-containing groups and compounds, such as haloalkyl, haloalkylthio, haloalkoxy, halocyclopropyl, haloalkenyl, haloalkynyl, haloallyloxy and haloallylthio, can be partly halogenated or perhalogenated, and in the case of multiple halogenation the halogen substituents can be identical or different. Examples of haloalkyl—as a group per se and as a structural element of other groups and compounds, such as of haloalkylthio and haloalkoxy—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which are mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl or one of its isomers which are mono- to nonasubstituted by fluorine, chlorine and/or bromine, such as $CF(CF_3)CHFCF_3$, $CF_2(CF_2)_2CF_3$ or $CH_2(CF_2)_2CF_3$. Examples of haloalkenyl are 2,2-difluoroethen-1-yl, 2,2-dichloroethen-1-yl, 2-chloroprop-1-en-3-yl, 2,3-dichloroprop-1-en-3-yl and 2,3-dibromoprop-1-en-3-yl. Examples of haloalkynyl are 2-chloroprop-1-yn-3-yl, 2,3-dichloroprop-1-yn-3-yl and 2,3-dibromoprop-1-yn-3-yl. Examples of halocyclopropyl are 2-chlorocyclopropyl, 2,2-difluorocyclopropyl and 2-chloro-2-fluoro-cyclopropyl. Examples of haloallyloxy are 2-chloroprop-1-en-3-yloxy, 2,3-dichloroprop-1-en-3-yloxy and 2,3-dibromoprop-1-en-3-yloxy. Examples of haloallylthio are 2-chloroprop-1-en-3-ylthio, 2,3-dichloroprop-1-en-3-ylthio and 2,3-dibromoprop-1-en-3-ylthio.

In phenylalkyl, an alkyl group bonded to the remaining part of the compound of the formula (A) is substituted by a phenyl group, the alkyl group preferably being straight-chain and the phenyl group preferably being bonded to the alkyl group in a position higher than the α-position, in particular in the ω-position; examples are benzyl, 2-phenylethyl and 4-phenyl-butyl.

Particularly preferred compounds of the formula (A) are those in which
(1) R is hydrogen, $C_1$-$C_4$alkyl, $C_3$-$C_6$cycloalkyl, $C_2$-$C_6$alkenyl or $C_2$-$C_6$alkynyl, in particular H or $CH_3$;
(2) the cyclic base skeleton of A contains 2 to 4, preferably conjugated, double bonds, preferably contains 2, preferably conjugated double bonds, and in particular has aromatic character,
(3) the cyclic base skeleton of A contains 1 up to and including 4, in particular 1 up to and including 3, especially 1 or 2, heteroatoms, particularly preferably 2 heteroatoms;
(4) the cyclic base skeleton of A contains 1, 2 or 3 heteroatoms chosen from the group consisting of oxygen, sulfur and nitrogen, not more than one of the heteroatoms contained in the cyclic base skeleton being an oxygen or sulfur atom, preferably at least one nitrogen atom;
(5) a compound of the formula (A), in which A is mono- or disubstituted by substituents chosen from the group consisting of halogen and $C_1$-$C_3$alkyl, in particular by halogen, especially by chlorine;
(6) a compound of the formula (A) in which the cyclic base skeleton of A is a pyridyl, 1-oxidopyridinio or thiazolyl group,
preferably the cyclic base skeleton of A is a pyrid-3-yl-, 1-oxido-3-pyridinio or thiazol-5-yl group,
in particular A is a pyrid-3-yl, 2-halopyrid-5-yl, 2,3-dihalopyrid-5-yl, 2-$C_1$-$C_3$alkylpyrid-5-yl, 1-oxido-3-pyridinio, 2-halo-1-oxido-5-pyridinio, 2,3-dihalo-1-oxido-5-pyridinio or 2-halothiazol-5-yl group,
A is especially a pyrid-3-yl, 2-halopyrid-5-yl, 2-halo-1-oxido-5-pyridinio or 2-halothiazol-5-yl group,
preferably A is a 2-chloropyrid-5-yl, 2-methylpyrid-5-yl, 1-oxido-3-pyridinio, 2-chloro-1-oxido-5-pyridinio, 2,3-dichloro-1-oxido-5-pyridinio or 2-chlorothiazol-5-yl group,
A is especially a pyrid-3-yl, 2-chloropyrid-5-yl, 2-chloro-1-oxido-5-pyridinio or 2-chlorothiazol-5-yl group,
in particular A is a 2-chloropyrid-5-yl or, preferably, 2-chlorothiazol-5-yl group
(7) a compound of the formula (A), in which X is N—$NO_2$;
(8) a compound of the formula (A), in which A is a 2-chlorothiazol-5-yl or 2-chloropyrid-5-yl group, R is $C_1$-$C_4$alkyl and X is N—$NO_2$.

Compounds of the formula (A) which are named as preferred in the context of the invention are
(A.1) (2-chloropyrid-5-ylmethyl)-3-methyl-4-nitroimino-perhydro-1,3,5-oxadiazine;
(A.2) (2-chlorothiazol-5-ylmethyl)-3-ethyl-4-nitroimino-perhydro-1,3,5-oxadiazine;
(A.3) 3-methyl-4-nitroimino-5-(1-oxido-3-pyridiniomethyl)-perhydro-1,3,5-oxadiazine;
(A.4) (2-chloro-1-oxido-5-pyridiniomethyl)-3-methyl-4-nitroimino-perhydro-1,3,5-oxadiazine;
(A.5) (2-chlorothiazol-5-ylmethyl)-3-methyl-4-nitroimino-perhydro-1,3,5-oxadiazine;
(A.6) 3-methyl-5-(2-methylpyrid-5-ylmethyl)-4-nitroimino-perhydro-1,3,5-oxadiazine;
(A.7) (2-chloropyrid-5-ylmethyl)-4-nitroimino-perhydro-1,3,5-oxadiazine;

(A.8) (2-chlorothiazol-5-ylmethyl)-4-nitroimino-perhydro-1,3,5-oxadiazine, or (A.9) (2-chloropyrid-5-ylmethyl)-3-ethyl-4-nitroimino-perhydro-1,3,5-oxadiazine.

5-(2-chlorothiazol-5-ylmethyl)-3-methyl-4-nitroimino-perhydro-1,3,5-oxadiazine is especially preferred in the context of the invention as the mixing partner of the formula (A). A composition which, in addition to the compound of the formula (A), also comprises only one further compound (I) to (CLXXXIV) having a pesticidal action is also preferred. Compositions which comprise pirimicarb in addition to a compound of the formula (A) are furthermore preferred. Compositions which comprise pyriproxyfen, fipronil, endosulfan or buprofezin in addition to a compound of the formula (A) are likewise preferred.

The active compound combination according to the invention preferably comprises the active compound of the formula (A) and one of the active compounds (I) to (CLXXXIV) in a mixing ratio of 100:1 to 1:6000, in particular 1:50 to 50:1, in particular in a ratio of between 1:20 and 20:1, in particular between 10:1 and 1:10, especially between 5:1 and 1:5, particularly preferably between 2:1 and 1:2, and also preferably between 4:1 and 2:1, especially in the ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or, 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. These ratios are understood as meaning weight ratios on the one hand, and also molar ratios on the other hand.

It has now been found, surprisingly, that the combination of the active compound of the formula (A) or of one of its salts with one of the active compounds (I) to (CLXXXIV) not only causes an additive increase in the action spectrum on the pests to be controlled, which is to be expected in principle, but that it achieves a synergistic effect which extends the action limits of both preparations under two aspects:

On the one hand, the rates of application of the compound of the formula (A) and of the individual compounds (I) to (CLXXXIV) are lowered for the same good action. On the other hand, the combined mixture also still has a high degree of pest control where the two individual substances have become completely inactive in the range of excessively low rates of application. This allows on the one hand a considerable extension to the spectrum of pests which can be controlled and on the other hand an increase in application reliability.

In addition to the actual synergistic action in respect of pesticidal activity, however, the compositions according to the invention also additionally have further surprising advantages which can likewise be described as synergistic in a broadened sense: thus, for example, it is possible to control pests which cannot be controlled or sufficiently effectively controlled with the individual compounds (A) or (I) to (CLXXXIV), and the compositions according to the invention show a better toleration by plants, i.e., for example, a reduced phytotoxicity, than the individual compounds (A) and (I) to (CLXXXIV). The insects can furthermore be controlled in their various stages of development, which sometimes is not the case with the individual compounds (A) and (I) to (CLXXXIV), since these compounds can be used, for example, only as adulticides or only as larvicides against quite specific larval stages. In addition, combinations of the compound (A) with certain compounds (I) to (CLXXXIV) show more favourable properties during grinding, mixing, storage and also spraying.

The compositions according to the invention are valuable preventively and/or curatively even at low rates of concentration in the field of pest control, while being tolerated by warm-blooded animals, fishes and plants, and have a very favourable biocidal spectrum. The compositions according to the invention are active against all or individual stages of development of normally sensitive and also resistant animal pests, such as insects and representatives of the order Acarina. The insecticidal and/or acaricidal action of the compositions according to the invention can manifest itself here directly, i.e. in a destruction of the pests, which occurs immediately or only after some time, for example during moulting, or indirectly, for example in a reduced oviposition and/or hatching rate, the good action corresponding to a rate of destruction (mortality) of at least 50 to 60%.

The animal pests include, for example:

from the order Lepidoptera

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., Hellula spp., *Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Oryzaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example

Blatta spp., Blattella spp., Gryllotalpa spp., *Leucophaea maderae*, Locusta spp., Periplaneta spp. and Schistocerca spp.;

from the order Isoptera, for example

Reticulitermes spp.;

from the order Psocoptera, for example

Liposcelis spp.;

from the order Anoplura, for example

Haematopinus spp., Linognathus spp., Pediculus spp., Pemphigus spp. and Phylloxera spp.;

from the order Mallophaga, for example

Damalinea spp. and Trichodectes spp.;

from the order Thysanoptera, for example

Frankliniella spp., Hercinothrips spp., Taeniothrips spp., *Thrips palmi, Thrips tabaci* and *Scirtothrips aurantii;* from the order Heteroptera, for example

Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.;

from the order Homoptera, for example
Aleurothrixus floccosus, Aleyrodes brassicae, Aonidiella spp., Aphididae, Aphis spp., Aspidiotus spp., Bemisia tabaci, Ceroplaster spp., Chrysomphalus aonidium, Chrysomphalus dictyospermi, Coccus hesperidum, Empoasca spp., Eriosoma lanigerum, Erythroneura spp., Gascardia spp., Laodelphax spp., Lecanium corni, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., Pulvinaria aethiopica, Quadraspidiotus spp., Rhopalosiphum spp., Saissetia spp., Scaphoideus spp., Schizaphis spp., Sitobion spp., Trialeurodes vaporariorum, Trioza erytreae and Unaspis citri;

from the order Hymenoptera, for example
Acromyrmex, Atta spp., Cephus spp., Diprion spp., Diprionidae, Gilpinia polytoma, Hoplocampa spp., Lasius spp., Monomorium pharaonis, Neodiprion spp., Solenopsis spp. and Vespa spp.;

from the order Diptera, for example
Aedes spp., Antherigona soccata, Bibio hortulanus, Calliphora erythrocephala, Ceratitis spp., Chrysomyia spp., Culex spp., Cuterebra spp., Dacus spp., Drosophila melanogaster, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., Oscinella frit, Pegomyia hyoscyami, Phorbia spp., Rhagoletis pomonelia, Sciara spp., Stomoxys spp., Tabanus spp., Tannia spp. and Tipula spp.;

from the order Siphonaptera, for example
Ceratophyllus spp. and Xenopsylla cheopis;

from the order Thysanura, for example
Lepisma saccharina and from the order Acarina, for example
Acarus siro, Aceria sheldoni, Aculus schlechtendali, Amblyomma spp., Argas spp., Boophilus spp., Brevipalpus spp., Bryobia praetiosa, Calipitrimerus spp., Chorioptes spp., Dermanyssus gallinae, Eotetranychus carpini, Eriophyes spp., Hyalomma spp., Ixodes spp., Olygonychus pratensis, Ornithodoros spp., Panonychus spp., Phyllocoptruta oleivora, Polyphagotarsonemus latus, Psoroptes spp., Rhipicephalus spp., Rhizoglyphus spp., Sarcoptes spp., Tarsonemus spp. and Tetranychus spp.

Using the active compound mixtures according to the invention, in particular pests of the type mentioned which occur on plants, especially useful plants and ornamentals in agriculture, in horticulture and in forestry, or on parts, such as fruit, blossom, foliage, stems, tubers, or roots, of such plants can be controlled, i.e. checked or destroyed, and in some cases parts of plants which additionally grow later are also still protected from these pests.

The pesticidal mixture according to the invention can advantageously be employed for pest control in cereals, such as maize or sorghum; in fruit, for example pome, stone and soft fruit, such as apples, pears, plums, peaches, almonds, cherries or berries, for example strawberries, raspberries and blackberries; in leguminous plants, such as beans, lentils, peas or soya; in oil-bearing crops, such as oilseed rape, mustard, poppy seed, olives, sunflower, coconut, castor, cacao or groundnuts; in gourds, such as pumpkins, cucumbers or melons; in fibre plants, such as cotton, flax, hemp or jute; in citrus fruits, such as oranges, lemons, grapefruits or mandarins; in vegetables, such as spinach, lettuce, asparagus, cabbage varieties, carrots, onions, tomatoes, potatoes or capsicum; in lauraceous plants, such as avocado, cinnamonium, camphor; or in tobacco, nuts, coffee, aubergines, sugar cane, tea, pepper, vines, hops, musaceous plants, natural rubber plants or ornamentals, in particular in maize, sorghum, pome and stone fruits, leguminous plants, cucurbits, cotton, citrus fruits, vegetables, aubergines, vines, hops or ornamentals, especially in maize, sorghum, apples, pears, plums, peaches, beans, peas, soya, olives, sunflower, coconut, cacao, groundnuts, cucumbers, pumpkins, citrus fruits, cabbage varieties, tomatoes, potatoes, vines or cotton,
particularly preferably in vines, citrus fruits, apples, pears, tomatoes and cotton.

Other fields of use of the active compound mixtures according to the invention are protection of stored products and stocks and of material, and in the hygiene sector, in particular the protection of domestic animals and productive livestock against pests of the type mentioned.

Depending on the aims to be achieved and the given circumstances, the pesticides according to the invention are emulsifiable concentrates, suspension concentrates, directly sprayable or dilutable solutions, spreadable pastes, dilute emulsions, sprayable powders, soluble powders, dispersible powders, wettable powders, dusts, granules or encapsulations in polymeric substances which comprise the compound of the formula (A) or one of its salts and one of the other active compounds (I) to (CLXXXIV) according to the invention.

The active compounds are employed in these compositions in a pure form, the solid active compounds, for example, being employed in a specific particle size, or, preferably, together with—at least—one of the auxiliaries conventionally used in the art of formulation, such as extenders, for example solvents or solid carriers, or such as surface-active compounds (surfactants).

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

Solid carriers, for example for dusts and dispersible powders, which are as a rule used are natural rock powders, such as calcite, talc, kaolin, montmorillonite or attapulgite. Highly disperse silicic acids or highly disperse absorbent polymers can also be added to improve the physical properties. Granular, adsorptive granule carriers are porous types, such as pumice, crushed brick, sepiolite or bentonite, and non-adsorptive carrier materials are calcite or sand. A large number of granulated materials of inorganic or organic nature, in particular dolomite or comminuted plant residues, can furthermore be used.

Surface-active compounds are, depending on the nature of the active compound to be formulated, nonionic, cationic and/or anionic surfactants or surfactant mixtures having good emulsifying, dispersing and wetting properties. The surfactants listed below are to be regarded only as examples here; many other surfactants which are conventionally used in the art of formulation and are suitable according to the invention are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol -ether groups and 8 to 20 carbon atoms in the (aliphatic) hydrocarbon radical and 6 to 18 carbon atoms in the alkyl radical of the alkylphenols. Water-soluble adducts, containing 20 to 250 ethylene glycol ether groups and 10 to 100 propylene glycol ether groups, of polyethylene oxide on polypropylene glycol, ethylenediaminopolypropylene glycol and alkylpolypropylene glycol having 1 to 10 carbon atoms in the alkyl chain are furthermore suitable. The compounds mentioned usually comprise 1 to 5 ethylene glycol units per propylene glycol unit. Examples are nonylphenol-polyethoxyethanols, castor oil polyglycol ether, polypropylene/polyethylene oxide adducts, tributylphenoxypolyethoxyethanol, polyethylene glycol and octylphenoxypolyethoxyethanol. Fatty acid esters of polyoxyethylene-sorbitan, such as polyoxyethylene-sorbitan trioleate, are furthermore possible.

Cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxy alkyl radicals. The salts are preferably in the form of halides, methyl-sulfates or ethyl-sulfates. Examples are stearyltrimethylammonium chloride and benzyldi(2-chloroethyl)ethylammonium bromide.

Suitable inorganic surfactants can be both water-soluble soaps and water-soluble synthetic surface-active compounds. Suitable soaps are the alkali metal, alkaline earth metal and substituted and unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts, and in general contain an alkyl radical having 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain two sulfonic acid groups and one fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, are furthermore also suitable.

The compositions as a rule comprise 0.1 to 99%, in particular 0.1 to 95%, of a mixture of the active compound of the formula (A) with one of the active compounds (I) to (CLXXXIV), and 1 to 99.9%, in particular 5 to 99.9%, of—at least—one solid or liquid auxiliary, where as a rule 0 to 25%, in particular 0.1 to 20%, of the compositions can be surfactants (% is in each case per cent by weight). While concentrated compositions are rather preferred as commercial goods, the end user as a rule uses dilute compositions which have considerably lower active compound concentrations. Preferred compositions have, in particular, the following composition (%=per cent by weight):

| Emulsifiable concentrates: | |
|---|---|
| Active compound mixture | 1 to 90%, preferably 5 to 20% |
| Surfactant: | 1 to 30%, preferably 10 to 20% |
| Solvent: | 5 to 98%, preferably 70 to 85% |
| Dusts: | |
| Active compound mixture: | 0.1 to 10%, preferably 0.1 to 1% |
| Solid carrier: | 99.9 to 90%, preferably 99.9 to 99% |
| Suspension concentrates: | |
| Active compound mixture: | 5 to 75%, preferably 10 to 50% |
| Water: | 94 to 24%, preferably 88 to 30% |
| Surfactant: | 1 to 40%, preferably 2 to 30% |
| Wettable powders: | |
| Active compound mixture: | 0.5 to 90%, preferably 1 to 80% |
| Surfactant: | 0.5 to 20%, preferably 1 to 15% |
| Solid carrier: | 5 to 99%, preferably 15 to 98% |
| Granules: | |
| Active compound mixture: | 0.5 to 30%, preferably 3 to 15% |
| Solid carrier: | 99.5 to 70%, preferably 97 to 85% |

The compositions according to the invention can also comprise other solid or liquid auxiliaries, such as, stabilizers, for example non-epoxidized or epoxidized plant oils (for example epoxidized coconut oil, rape oil or soya oil), defoamers, for example silicone oil, preservatives, viscosity regulators, binders and/or tackifiers, as well as fertilizers or other active compounds for achieving specific effects, for example bactericides, fungicides, nematicides, mollusicides or herbicides.

The compositions according to the invention are prepared in a known manner, in the absence of auxiliaries, for example, by grinding, sieving and/or pressing a solid active compound or active compound mixture, for example to a particular particle size, and in the presence of at least one auxiliary, for example, by intimate mixing and/or grinding of the active compound or active compound mixture with the auxiliary or auxiliaries. The invention therefore also relates to the process for the preparation of the compositions.

Mixtures of a compound of the formula (A) with one or more of the compounds (I) to (CLXXXIV) are preferably employed with the auxiliaries conventionally used in the art of formulation, and are therefore processed, for example, to emulsifiable concentrates, directly sprayable or dilutable solutions, dilute emulsions, wettable powders, soluble powders, dusts and granules, and also to encapsulations in, for example, polymeric substances, in a known manner. The methods of application, such as spraying, atomizing, dusting, wetting, scattering or pouring are chosen, as is the nature of the composition, according to the aims to be achieved and the given circumstances.

The invention furthermore relates to the methods of application for the compositions, i.e. the methods for controlling pests of the type mentioned, such as spraying, atomizing, dusting, spreading, dressing, scattering or pouring, to be chosen according to the aims to be achieved and the given circumstances, and the use of the compositions for controlling pests of the type mentioned. Typical rates of concentration here are between 0.1 and 1000 ppm, preferably between 0.1 and 500 ppm, of active compound. The rate of application can vary within wide limits and depends on the nature of the soil, the nature of the application, (leaf application; seed dressing, application in the seed furrow), the crop plant, the pest to be controlled, the particular climatic circumstances which prevail and other factors determined by the nature of the application, the time of application and the target crop. The rates of application per hectare are in general 1 to 2000 g of active compound per hectare, in particular 10 to 1000 g/ha, preferably 20 to 600 g/ha.

A preferred method of application in the field of crop protection is application to the foliage of the plants (leaf application), where the frequency of application and rate of application can be chosen according to the risk of infestation by the particular pest. However, the active compound can also enter the plants via the root system (systemic action) by impregnating the locus of the plants with a liquid composition or introducing the active compounds in solid form into the locus of the plants, for example into the soil, for example in the form of granules (soil application). In paddy rice crops, such granules can be metered onto the flooded rice field.

The compositions according to the invention are also suitable for the protection of plant propagation material, for example seeds, such as fruit, tubers, or grain, or plant seedlings, against animal pests. The propagation material can be treated with the composition before being brought out, for example seed can be dressed before sowing. The active compounds according to the invention can also be applied to the seed grains (coating) either by impregnating the grains in a liquid composition or coating them with a solid composition. The composition can also be applied to the site where the propagation material is brought out, during broadcasting, for example into the seed furrow during sowing. The invention furthermore relates to the treatment methods for plant propagation material and the plant propagation material treated in this way.

The following examples serve to illustrate the invention. They do not limit the invention.

FORMULATION EXAMPLES (%=% by Weight, Active Compound Ratios=Weight Ratios)

EXAMPLE F1

| Emulsion concentrates | | | |
|---|---|---|---|
| | a) | b) | c) |
| Active compound mixture (Compound (A): Compound (I) to (CLXXXIV) = 1:1) | 25% | 40% | 50% |
| Ca dodecylbenzenesulfonate | 5% | 8% | 6% |
| Castor oil polyethylene glycol ether (36 mol of EO) | 5% | | |
| Tributylphenolpolyethylene glycol ether (30 mol of EO) | | 12% | 4% |
| Cyclohexanone | | 15% | 20% |
| Xylene mixture | 65% | 25% | 20% |

EO is the degree of ethoxylation of castor oil or tributylphenol.

Emulsions of any desired concentration can be prepared from such concentrates by dilution with water.

EXAMPLE F2

| Solutions | | | | |
|---|---|---|---|---|
| | a) | b) | c) | d) |
| Active compound mixture (Compound (A): Compound (I) to (CLXXXIV) = 1:3) | 80% | 10% | 5% | 95% |
| Ethylene glycol monomethyl ether | | 20% | | |
| Polyethylene glycol molecular wt. 400 | | 70% | | |
| N-methyl-2-pyrrolidone | 20% | | | |
| Epoxidized coconut oil | | | 1% | 5% |
| Benzine (boiling limits 160-190° C.) | | | 94% | |

The solutions are suitable for use in the form of tiny drops.

EXAMPLE F3

| Granules | | | | |
|---|---|---|---|---|
| | a) | b) | c) | d) |
| Active compound mixture (Compound (A): Compound (I) to (CLXXXIV) = 3:1) | 5% | 10% | 8% | 21% |
| Kaolin | 94% | | 79% | 54% |
| Highly disperse silicic acid | 1% | | 13% | 7% |
| Attapulgite | | 90% | | 18% |

The active compounds are dissolved together in methylene chloride, the solution is sprayed onto the carrier and the solvent is then evaporated off in vacuo.

EXAMPLE F4

| Dusts | | |
|---|---|---|
| | a) | b) |
| Active compound mixture (1:1) | 2% | 5% |
| Highly disperse silicic acid | 1% | 5% |
| Talc | 97% | |
| Kaolin | | 90% |

Intimate mixing of the carriers with the active compounds gives ready-to-use dusts.

EXAMPLE F5

| Wettable powders | | | |
|---|---|---|---|
| | a | b) | c) |
| Active compound mixture (Compound (A): Compound (I) to (CLXXXIV) = 4:1) | 25% | 50% | 75% |
| Sodium ligninsulfonate | 5% | 5% | |
| Sodium lauryl sulfate | 3% | | 5% |
| Sodium diisobutylnaphthalene-sulfonate | | 6% | 10% |
| Octylphenol polyethylene glycol-ether (7-8 mol of EO) | | 2% | — |
| Highly disperse silicic acid | 5% | 10% | 10% |
| Kaolin | 62% | 27% | — |

The active compounds are mixed with the additives and ground thoroughly in a suitable mill. Wettable powders which can be diluted with water to give suspensions of any desired concentration are obtained.

EXAMPLE F6

| Emulsion concentrate | |
|---|---|
| Active compound mixture (1:2) | 10% |
| Octylphenol polyethylene glycol ether (4-5 mol of EO) | 3% |
| Calcium dodecylbenzenesulfonate | 3% |
| Castor oil polyglycol ether (36 mol of EO) | 4% |
| Cyclohexanone | 30% |
| Xylene mixture | 50% |

Emulsions of any desired concentration can be prepared from this concentrate by dilution with water.

EXAMPLE F7

| Dusts | | |
|---|---|---|
| | a) | b) |
| Active compound mixture (Compound (A): Compound (I) to (CLXXXIV) = 2:5) | 5% | 8% |
| Talc | 95% | — |
| Kaolin | | 92% |

Ready-to-use dusts are obtained by mixing the active compounds with the carrier and grinding the mixture on a suitable mill.

EXAMPLE F8

| Extruded granules | |
|---|---|
| Active compound mixture (2:1) | 10% |
| Sodium ligninsulfonate | 2% |
| Carboxymethylcellulose | 1% |
| Kaolin | 87% |

The active compounds are mixed with the additives and the mixture is ground and moistened with water. This mixture is extruded, granulated and then dried in a stream of air.

EXAMPLE F9

| Coated granules | |
|---|---|
| Active compound mixture (1:1) | 3% |
| Polyethylene glycol (molecular wt. 200) | 3% |
| Kaolin | 94% |

The finely ground active compounds are applied uniformly to the kaolin, which is moistened with polyethylene glycol, in a mixer. Dust-free coated granules are obtained in this way.

EXAMPLE F10

| Suspension concentrate | |
|---|---|
| Active compound mixture (1:1) | 40% |
| Ethylene glycol | 10% |
| Nonylphenol polyethylene glycol ether (15 mol of EO) | 6% |
| Sodium ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active compounds are mixed intimately with the additives. A suspension concentrate from which suspensions of any desired concentration can be prepared by dilution with water is thus obtained.

It is often more practical to formulate the active compound of the formula (A) and one of the mixing partners (I) to (CLXXXIV) individually and then to bring them together in the applicator in the desired mixing ratio as "tank mixing" in the water only shortly before application.

BIOLOGICAL EXAMPLES (%=Per Cent by Weight, Unless Stated Otherwise)

A synergistic effect is always present if the action EA of the combination of an active compound of the formula (A) with one of the active compounds (I) to (CLXXXIV) is greater than the sum of the action of the active compounds applied individually:

$$EA_1 > X + Y \quad (B)$$

However, the pesticidal action EA to be expected for a given combination of two pesticides can also be calculated as follows (cf. COLBY, S. R., "Calculating synergistic and antagonistic response of herbicide combinations", Weeds 15, Pages 20-22, 1967).

In this equation:

$$EA_2 = X + \frac{Y(100-X)}{100}$$

X=Per cent mortality on treatment with the compound of the formula (A) at a rate of application of p kg per hectare compared with the untreated control (=0%).

Y=Per cent mortality on treatment with a compound (I) to (CLXXXIV) at a rate of application of q kg per hectare compared with the untreated control.

EA=Expected pesticidal action (per cent mortality compared with the untreated control) after treatment with the compound of the formula (A) and a compound (I) to (CLXXXIV) at a rate of application of p+q kg of active compound per hectare.

If the action actually observed is greater than the expected value EA, synergism exists.

Example B1

Action Against *Bemisia tabaci*

Dwarf bean plants are placed in gauze cages and populated with adults of *Bemisia tabaci*. After oviposition has taken place, all the adults are removed. 10 days later, the plants with the nymphs on them are sprayed with an aqueous suspension spray liquor comprising 50 ppm of the active compound mixture. After a further 14 days, the percentage hatching of the eggs is evaluated in comparison with untreated control batches.

In this test, the combinations of an active compound of the formula (A) with one of the active compounds (I) to (CLXXXIV) show a synergistic effect. In particular, a suspension spray liquor which comprises 40 ppm of the compound (A.5) and 10 ppm of the compound (II) shows an activity of over 80%.

Example B2

Action Against *Spodoptera littoralis* Caterpillars

Young soya plants are sprayed with an aqueous emulsion spray liquor comprising 360 ppm of the active compound mixture. After the spray coating has dried on, the soya plants are populated with 10 caterpillars of the third stage of *Spodoptera littoralis* and placed in a plastic container. Evaluation takes place 3 days later. The percentage reduction in the population and the percentage reduction in feeding damage (% action) are determined from comparison of the number of dead caterpillars and of the feeding damage on the treated plants to those on the untreated plants.

In this test, combinations of an active compound of the formula (A) with one of the active compounds (I) to (CLXXXIV) show a synergistic effect. In particular, a suspension spray liquor which comprises 200 ppm of the compound (A.2) and 160 ppm of the compound (XXIX) and a suspension spray liquor which comprises 120 ppm of the compound (A) and 240 ppm of the compound (XXIV) show an activity of over 80%.

Example B3

Ovizidal Action on *Lobesia botrana*

*Lobesia botrana* eggs deposited on filter paper are immersed for a short time in an acetone-aqueous test solution comprising 400 ppm of the active compound mixture to be tested. After the test solution has dried on, the eggs are incubated in Petri dishes. After 6 days, the percentage hatching of the eggs is evaluated in comparison with untreated control batches (% reduction in hatching).

In this test, combinations of an active compound of the formula (A) with one of the active compounds (I) to (CLXXXIV) show a synergistic effect. In particular, a suspension spray liquor which comprises 300 ppm of the compound (A.5) and 100 ppm of the compound (III) and a suspension spray liquor which comprise 200 ppm of the compound (A.2) and 200 ppm of the compound (LVII) show an activity of over 80%.

Example B4

Ovizidal Action on *Heliothis virescens*

*Heliothis virescens* eggs deposited on filter paper are immersed for a short time in an acetone-aqueous test solution comprising 400 ppm of the active compound mixture to be tested. After the test solution has dried on, the eggs are incubated in Petri dishes. After 6 days, the percentage hatching of the eggs is evaluated in comparison with untreated control batches (% reduction in hatching).

In this test, combinations of an active compound of the formula (A) with one of the active compounds (I) to (CLXXXIV) show a synergistic effect. In particular, a suspension spray liquor which comprises 240 ppm of the compound (A.1) and 160 ppm of the compound (l) and a suspension spray liquor which comprise 100 ppm of the compound (A.5) and 300 ppm of the compound (l) show an activity of over 80%.

Example B5

Action Against *Plutella xylostella* Caterpillars

Young cabbage plants are sprayed with an aqueous emulsion spray liquor which comprises 440 ppm of the active compound. After the spray coating has dried on, the cabbage plants are populated with ten caterpillars of the third stage of *Plutella xylostella* and placed in a plastic container. The evaluation takes place 3 days later. The percentage reduction in population and percentage reduction in feeding damage (% action) are determined from the comparison of the number of dead caterpillars and of the feeding damage on the treated plants to those on the untreated plants.

In this test, combinations of an active compound of the formula (A) with one of the active compounds (I) to (CLXXXIV) show a synergistic effect. In particular, a suspension spray liquor which comprises 40 ppm of the compound (A.5) and 400 ppm of the compound (XI) and a suspension spray liquor which comprises 220 ppm of the compound (A.7) and 220 ppm of the compound (L) show an activity of over 80%.

Example B6

Action Against *Myzus persicae*

Pea seedlings are infected with *Myzus persicae*, subsequently sprayed with a spray liquor comprising 400 ppm of the active compound and incubated at 20° C. An evaluation takes place 3 and 6 days later. The percentage reduction in the population (% action) is determined from the comparison of the number of dead aphids on the treated plants to that on the untreated plants.

In this test, combinations of an active compound of the formula (A) with one of the active compounds (I) to (CLXXXIV) show a synergistic effect. In particular, a suspension spray liquor which comprises 1 ppm of the compound (A.5) and 40 ppm of pirimicarb and a suspension spray liquor which comprises 0.2 ppm of the compound (A.5) and 75 ppm of pirimicarb show an activity of over 80%*.

What is claimed is:

1. A synergistic composition for controlling insects, the composition comprising thiamethoxam and abamectin, wherein the weight ratio of thiamethoxam to abamectin is from about 10:1 to about 1:1; and wherein said composition provides an insecticidal synergistic effect.

2. Plant propagation material treated with the composition defined in claim 1.

3. Plant propagation material according to claim 2, wherein the plant propagation material is a seed.

4. The composition according to claim 1, wherein the weight ratio of thiamethoxam to abamectin is from 5:1 to 1:1.

* * * * *